United States Patent
Dickerson

(10) Patent No.: US 10,175,096 B2
(45) Date of Patent: Jan. 8, 2019

(54) SYSTEM AND METHOD TO ENABLE RE-USE OF SURGICAL INSTRUMENT

(71) Applicant: Ethicon Endo-Surgery, LLC, Guaynabo, PR (US)

(72) Inventor: Benjamin D. Dickerson, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 85 days.

(21) Appl. No.: 15/088,398

(22) Filed: Apr. 1, 2016

(65) Prior Publication Data
US 2017/0284860 A1    Oct. 5, 2017

(51) Int. Cl.
*A61B 5/00* (2006.01)
*A61B 5/04* (2006.01)
(Continued)

(52) U.S. Cl.
CPC .............. *G01H 15/00* (2013.01); *A61B 5/00* (2013.01); *A61B 17/320092* (2013.01); *A61B 90/08* (2016.02); *A61B 18/1445* (2013.01); *A61B 2017/00725* (2013.01); *A61B 2018/00988* (2013.01); *A61B 2090/0803* (2016.02); *A61B 2090/0809* (2016.02)

(58) Field of Classification Search
CPC ........ G01H 15/00; A61B 90/08; A61B 90/03; A61B 90/98; A61B 17/072; A61B 17/068; A61B 17/07207; A61B 17/320092; A61B 17/320068; A61B 5/00; A61B 5/1464
See application file for complete search history.

(56) References Cited

U.S. PATENT DOCUMENTS 5,322,055 A    6/1994  Davison et al.
5,400,267 A *  3/1995  Denen .................... A61B 17/00
                                                128/908
(Continued)

FOREIGN PATENT DOCUMENTS

WO    WO 2015/157436 A1    2/2015

OTHER PUBLICATIONS

International Search Report and Written Opinion dated Jun. 7, 2017 for International Application No. PCT/US2017/025003, 8 pages.

*Primary Examiner* — Helen Kwok
(74) *Attorney, Agent, or Firm* — Frost Brown Todd LLC

(57) ABSTRACT

Some surgical instruments become partially or fully disabled at a device firmware level after being used in a surgical procedure in order to prevent overuse or abuse of the surgical instrument that could create patient safety concerns. A reconditioning device may be used by the end user of such a surgical instrument to perform diagnostics and reconditioning of the surgical instrument so that the surgical instrument may be placed back into service without the direct intervention of the manufacturer. The reconditioning device provides power to the surgical instrument, analyzes device usage history, activates and tests the surgical instrument cutting and gripping functions, and measures electrical characteristics and mechanical characteristics of the surgical instrument. Gathered data is used to determine if the surgical instrument may be safely reconditioned for further use. If reconditioning is possible, the device will be reconfigured for safe use, reactivated, and then sterilized for subsequent re-use.

18 Claims, 9 Drawing Sheets

(51) Int. Cl.
    *A61B 5/0215*      (2006.01)
    *G01H 15/00*      (2006.01)
    *A61B 90/00*      (2016.01)
    *A61B 17/32*      (2006.01)
    *A61B 18/14*      (2006.01)
    *A61B 17/00*      (2006.01)
    *A61B 18/00*      (2006.01)

(56) References Cited

U.S. PATENT DOCUMENTS

| | | | |
|---|---|---|---|
| 5,720,293 A * | 2/1998 | Quinn | A61B 5/028 600/505 |
| 5,873,873 A | 2/1999 | Smith et al. | |
| 5,938,633 A * | 8/1999 | Beaupre | A61B 17/320068 604/22 |
| 5,980,510 A | 11/1999 | Tsonton et al. | |
| 6,325,811 B1 | 12/2001 | Messerly | |
| 6,553,241 B2 * | 4/2003 | Mannheimer | A61B 5/14552 600/323 |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,393,037 B2 | 7/2016 | Olson et al. | |
| 9,445,723 B2 * | 9/2016 | Hoffman | H04L 9/3242 |
| 9,724,094 B2 * | 8/2017 | Baber | A61B 17/072 |
| 2005/0283210 A1 * | 12/2005 | Blischak | A61M 5/14276 607/60 |
| 2006/0079874 A1 | 4/2006 | Faller et al. | |
| 2006/0161054 A1 * | 7/2006 | Reuss | A61B 5/00 600/300 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0030311 A1 * | 1/2009 | Stulen | A61B 17/320092 600/439 |
| 2009/0143806 A1 | 6/2009 | Witt et al. | |
| 2011/0155781 A1 * | 6/2011 | Swensgard | A61B 17/07207 227/176.1 |
| 2012/0078243 A1 | 3/2012 | Worrell et al. | |
| 2013/0023875 A1 * | 1/2013 | Harris | A61B 18/1445 606/47 |
| 2015/0053748 A1 * | 2/2015 | Yates | A61B 34/74 227/180.1 |
| 2015/0141981 A1 | 5/2015 | Price et al. | |
| 2015/0272575 A1 * | 10/2015 | Leimbach | A61B 17/072 227/175.3 |
| 2015/0272579 A1 * | 10/2015 | Leimbach | A61B 17/07207 227/178.1 |
| 2015/0303996 A1 * | 10/2015 | Calderoni | A61B 90/98 307/104 |
| 2017/0000552 A1 * | 1/2017 | Asher | A61B 18/14 |

\* cited by examiner

SYSTEM AND METHOD TO ENABLE RE-USE OF SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jul. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, now U.S. Pat. No. 9,393,037, issued Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein.

As a result of the critical nature of procedures performed with surgical instruments, extremely tight tolerances may be required both for newly manufactured instruments as well as for reusable instruments that have previously been put into service. While a particular surgical instrument may meet or exceed a specification at the time of manufacture, its performance may degrade after several uses due to normal wear and tear, or due to expansion of parts as a result of heat sterilization between uses. While manufacturers of such a product my provide guidelines for a number of uses before an instrument should be disposed, cost conscious end users may ignore such guidelines and create safety risks and other undesirable issues for end users and patients.

While a variety of systems have been made and used for surgical instrument lifecycle management, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Surgical Instrument

Figure 1:
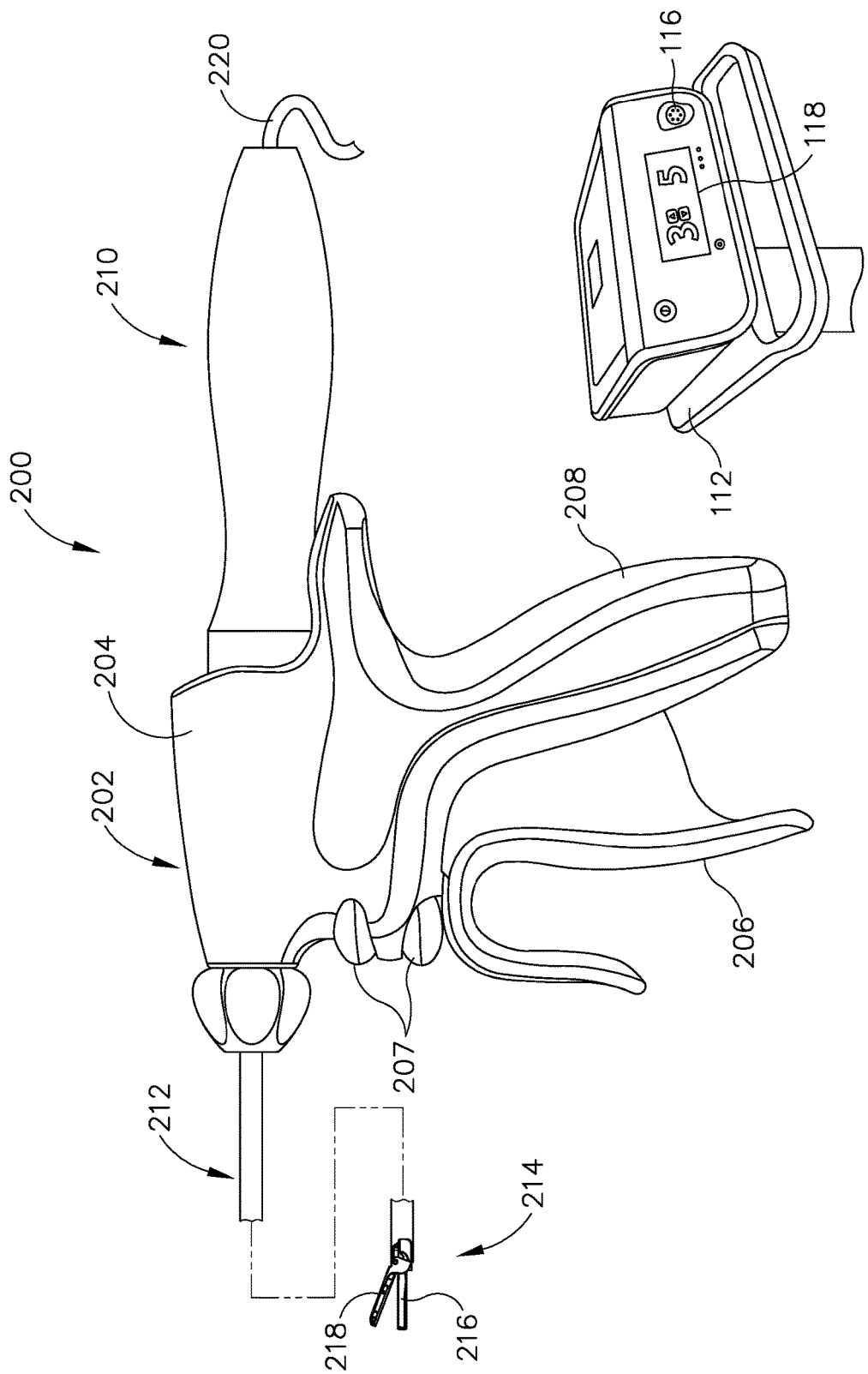
FIG. 1 depicts a side elevation view of an exemplary surgical instrument.

FIG. 1 shows a side elevation view of an exemplary surgical instrument (200). Instrument (200) is configured to be used as a set of ultrasonic shears, such that instrument (200) is operable to cut tissue and seal or weld tissue substantially simultaneously. It should also be understood that instrument (200) may have various structural and functional similarities with the HARMONIC ACE® Ultrasonic Shears by Ethicon Endo-Surgery, Inc. of Cincinnati, Ohio. Furthermore, instrument (200) may have various structural and functional similarities with the devices taught in any of the other references that are cited and incorporated by reference herein.

Instrument (200) of this example comprises a handle assembly (202), a shaft assembly (212), and an end effector (214). Handle assembly (202) comprises a body (204) including a pistol grip (208) and buttons (207). Handle assembly (202) also includes a trigger (206) that is pivotable toward and away from pistol grip (208). It should be understood, however, that various other suitable configurations may be used, including but not limited to a pencil-grip configuration or a scissor-grip configuration. By way of further example only, instrument (200) may be configured and operable like the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio.

An ultrasonic transducer assembly (210) extends proximally from body (204) of handle assembly (202). In some versions, transducer assembly (210) is removable relative to body (204). In some other versions, transducer assembly (210) is fully contained within body (204) or is otherwise permanently affixed to body (204). Transducer assembly (210) is coupled with a generator (112) via a cable (220) (only a portion of which is shown in FIG. 1), which is connected to a receptacle assembly (116) of generator (112). Transducer assembly (210) receives electrical power from generator (112) and converts that power into ultrasonic vibrations through piezoelectric elements. Transducer assembly (210) is activated in response to actuation of one of buttons (207). Receptacle assembly (116) provides a power and/or data input/output for connecting surgical instrument (200) to the generator (112). Generator (112) of the present example further includes a display (118). Display (118) provides information on the generator (112) and any attached surgical instrument (200). In some versions, display (118) further provides controls or interfaces for allowing a user to change various settings of generator (112). Generator (112) further includes a power source and control module that is configured to provide a power profile to transducer assembly (102) that is particularly suited for the generation of ultrasonic vibrations through transducer assembly (210). Other configurations for transducer assembly (210) exist and will be apparent to those of ordinary skill in the art in view of the teachings herein.

By way of example only, generator (112) may comprise a GEN 04 or GEN 11 sold by Ethicon Endo-Surgery, Inc. of Cincinnati, Ohio. In addition or in the alternative, generator (112) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. Still other suitable forms that generator (112) may take, as well as various features and operabilities that generator (112) may provide, will be apparent to those of ordinary skill in the art in view of the teachings herein.

End effector (214) includes an ultrasonic blade (216) and a pivoting clamp arm (218). Clamp arm (218) is coupled with trigger (206) such that clamp arm (218) is pivotable toward ultrasonic blade (216) in response to pivoting of trigger (206) toward pistol grip (208); and such that clamp arm (218) is pivotable away from ultrasonic blade (216) in response to pivoting of trigger (206) away from pistol grip (208). Various suitable ways in which clamp arm (218) may be coupled with trigger (206) will be apparent to those of ordinary skill in the art in view of the teachings herein.

Blade (216) of the present example is operable to vibrate at ultrasonic frequencies in order to effectively cut through and seal tissue, particularly when the tissue is being compressed between clamp arm (218) and blade (216). Blade (216) is positioned at the distal end of an acoustic drivetrain. This acoustic drivetrain includes transducer assembly (210) and an acoustic waveguide (not shown) extending between transducer assembly (210) and blade (216). Transducer assembly (210) includes a set of piezoelectric elements (not shown) that are located proximal to a horn (not shown) of the rigid acoustic waveguide. The piezoelectric discs are operable to convert electrical power into ultrasonic vibrations, which are then transmitted along acoustic waveguide, which extends through shaft assembly (212), to blade (216) in accordance with known configurations and techniques. By way of example only, this portion of the acoustic drivetrain may be configured in accordance with the teachings above and/or various teachings of various references that are cited herein. When ultrasonic blade (216) is in an activated state (i.e., vibrating ultrasonically), ultrasonic blade (216) is operable to effectively cut through and seal tissue, particularly when the tissue is being compressed between clamp arm (218) and ultrasonic blade (216).

In some versions, end effector (214) is operable to apply radiofrequency (RF) electrosurgical energy to tissue in addition to applying ultrasonic energy to tissue. By way of example only, end effector (214) may be configured and operable in accordance with at least some of the teachings of U.S. Pub. No. 2015/0141981, entitled "Ultrasonic Surgical Instrument with Electrosurgical Feature," published May 21, 2015, now U.S. Pat. No. 9,949,785, issued Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein. Other suitable configurations for an acoustic transmission assembly and transducer assembly (210) will be apparent to one or ordinary skill in the art in view of the teachings herein. Similarly, other suitable configurations for end effector (214) will be apparent to those of ordinary skill in the art in view of the teachings herein.

II. Exemplary Surgical Instrument Reconditioning Device

Figure 2:
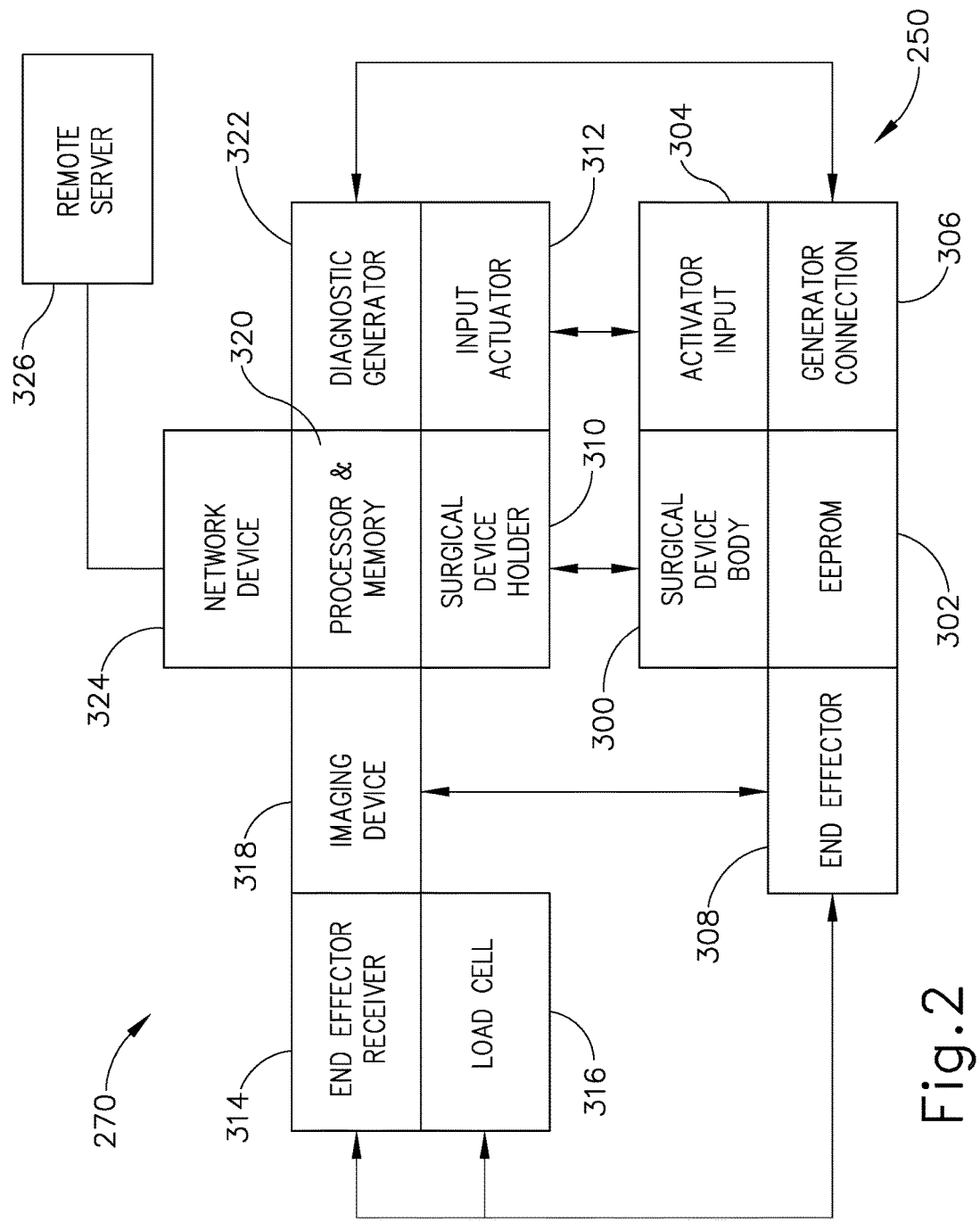
FIG. 2 depicts a schematic diagram of an exemplary surgical instrument and an exemplary reconditioning device.

Some versions of instrument (200) are configured such that instrument (200) is fully or partially disabled after instrument (200) has been used in a surgical procedure. However, in some instances, after instrument (200) is used in one surgical procedure, it may be desirable to permit instrument (200) to be reprocessed, sterilized, and reused in a subsequent surgical procedure. It may nevertheless also be desirable to provide some degree of restriction and/or quality control on the reprocessing and re-use of instrument (200) in order to ensure patient safety. To that end, FIG. 2 shows an exemplary surgical instrument (250) interfacing with an exemplary diagnostic and reconditioning device (270). In the present example, surgical instrument (250) is substantially identical to instrument (200) described above. However, it should be understood that the use of an ultrasonic surgical instrument in this example is merely illustrative. By way of further example only, instrument (250) may alternatively comprise an RF electrosurgical instrument (e.g., similar to the ENSEAL® electrosurgical instrument by Ethicon Endo-Surgery, Inc. of Cincinnati, Ohio), a surgical stapler (e.g., similar to the ECHELON® stapling instrument by Ethicon Endo-Surgery, Inc. of Cincinnati, Ohio), and/or any other suitable kind of surgical instrument. Various other kinds of instruments with which the teachings herein may be readily applied will be apparent to those of ordinary skill in the art.

Diagnostic and reconditioning device (270) may be provided as a piece of capital equipment whose actual design may vary by the specific setting it will be used in and the kind(s) of surgical instruments (250) that diagnostic and reconditioning device (270) will be compatible with. For example, in some versions diagnostic and reconditioning device (270) may be a single piece of equipment that is permanently installed at a location, may be mounted on a cart for relocation, or may be integrated with another piece of equipment, such as a generator (112), a surgical instrument sanitizing station (e.g., similar to the STERRAD® sterilization system by Advanced Sterilization Products of Irvine, Calif.), or a surgical instrument storage rack. As another example, diagnostic and reconditioning device (270) could also be a number of modular components that may be variably connected to a central device, such as a generator (112) or a specially designed proprietary piece of equipment to allow for flexible reconfiguration in order to provide reconditioning for a variety of devices. Various other suitable ways in which diagnostic and reconditioning device (270) may be embodied will be apparent to those of ordinary skill in the art in view of the teachings herein.

As shown in FIG. 2, surgical instrument (250) has a surgical device body (300) that houses an EEPROM (302). The EEPROM (302) may store various usage data for surgical instrument (250) that is generated when surgical instrument (250) is during a surgical procedure. Such usage data could include the number of times surgical instrument (250) is activated, which features of surgical instrument (250) are used, how long surgical instrument (250) is connected to a generator (112), the number of times each individual button (207) and/or feature(s) of the surgical instrument (250) is/are activated, model number and serial numbers of other devices that are paired with instrument (250) (e.g., generators (112) or transducer assemblies (210), etc.), custom user entered data such as procedures that surgical instrument (250) is used in or a physician's observations of the performance of surgical instrument (250), and other similar information. The EEPROM (302) may also contain various operational configurations for surgical instrument (250), such as configurations indicating whether certain features of surgical instrument (250) are disabled, software enforced safety mechanisms that may cause surgical instrument (250) to be non-operational in certain conditions, electrical and mechanical limitations on surgical instrument (250) to control the electrical power supplied to surgical instrument (250) or the mechanical output of surgical instrument (250), and similar configurations.

An activation input (304) is located on body (300) and may be in the form of a trigger like trigger (206) shown in FIG. 1, a button like buttons (207) shown in FIG. 1, a switch, a lever, or any other type of activation input that may desirably be included on a surgical instrument. Also located on the body (300) is a generator connection (306) that allows surgical instrument (250) to be connected to a generator (112) so that power may be provided to surgical instrument (250); and also so that data may be read from or written to the EEPROM (302) in order to update usage data, modify operational configurations, or the like. Also extending from device body (300) is an end effector (308) that may include one or more of a clamp arm (e.g., similar to clamp arm (218)), an ultrasonic blade (e.g., similar to blade (216)), and/or another feature that is operable to cut, seal, staple, grip, and/or otherwise manipulate tissue.

Diagnostic and reconditioning device (270) has a surgical device holder (310) that is configured to receive, grip, or immobilize a portion of surgical device body (300) and thereby support and hold surgical instrument (250) steady when surgical instrument (250) is inserted or attached to diagnostic and reconditioning device (270). Also present is an input actuator (312) that is configured be placed proximate to activation input (304) and, depending on the type of activation input (304) present, extend, recede, contract, expand, or otherwise move in order to cause activation input (304) to be actuated. By way of example only, input actuator (312) may comprise a motor, a solenoid, and/or any other kind of component that is operable to produce actuating movement in response to a control signal. Depending on the particular form of surgical instrument (250), there may be several activation inputs (304) that activate different features of surgical instrument (250). As a result, some versions of diagnostic and reconditioning device (270) may have several input actuators (312), so that each feature of surgical instrument (250) may be selectively activated. Referring back to surgical instrument of FIG. 1, diagnostic and reconditioning device (270) may have a first input actuator (312) that is operable to actuate trigger (206), a second input actuator (312) that is operable to actuate one button (207), and another input actuator (312) that is operable to actuate the other button (207). Various suitable forms and arrangements that may be used for input actuator (312) will be apparent to those of ordinary skill in the art in view of the teachings herein.

Diagnostic and reconditioning device (270) also has an end effector receiver (314), which is configured to receive end effector (308) of the attached surgical instrument (250). For example, in a version of diagnostic and reconditioning device (270) that is compatible for use with a surgical instrument (200) having an ultrasonic blade (216), end effector receiver (314) may comprise an optical or laser sensor that may be focused on ultrasonic blade (216) during operation so that vibration frequency or intensity may be measured without damaging ultrasonic blade (216). Also present may be a load cell (316) sensor that may be used to test the grip strength, consistency, and speed of clamp arm (218). Load cell (316) may comprise a plate (e.g., formed of metal and/or plastic, etc.), with a surface sized and textured for effective gripping by clamp arm (218), and having an embedded pressure sensor or load cell positioned to measure forces applies to the load cell (316) surface. The particular configuration or presence of end effector receiver (314) and load cell (316) will depend upon the kind of surgical instrument (250) being connected to diagnostic and reconditioning device (270). Thus, some versions of diagnostic and reconditioning device (270) may be modular in nature and may allow for different types of end effector receiver (314) to be attached to the rest of diagnostic and reconditioning device (270) or removed from the rest of diagnostic and reconditioning device (270), allowing for a variety of testing configurations. Various suitable forms and arrangements that may be used for end effector receiver (314) will be apparent to those of ordinary skill in the art in view of the teachings herein.

Diagnostic and reconditioning device (270) of the present example also includes an imaging device (318), such as a two dimensional or three dimensional camera or other image capturing device. Imaging device (318) may be placed to visually observe end effector (308), device body (300), activation input (304) and/or other features of surgical instrument (250) during connection to diagnostic and reconditioning device (270) and test operation so that present physical condition and operational variance of surgical instrument (250) may be compared against original specifications. It should therefore be understood that imaging device (318) may be used to provide machine vision to sense the condition of surgical instrument (250). Referring back to instrument (200) as an illustrative example, imaging device (318) may be used to visually observe the condition of a clamp pad on clamp arm (218) to determine whether the clamp pad has been worn beyond an acceptable degree, which would warrant replacement of the clamp pad; or if the clamp pad has an acceptable degree of wear. As another merely illustrative example using instrument (200), imaging device (318) may be used to confirm whether clamp arm (218) is still appropriately aligned with blade (216); and if clamp arm (218) travels along an appropriate closure path in response to actuation of trigger (206). As yet another merely illustrative example using instrument (200), imaging device (318) may be used to determine whether blade (216) has any cracks, nicks, or other unacceptable conditions.

In addition or in the alternative, imaging device (318) may be used to provide machine vision to ensure that surgical instrument (250) is properly seated in diagnostic and reconditioning device (270), to identify the kind of surgical instrument (250) or otherwise identify surgical instrument (250), and/or for other purposes. By way of further example only, imaging device (318) may be configured to read an identifying optical code (e.g., QR code, barcode, etc.) on surgical instrument (250). As another example, imaging device (318) may also be used to guide and optimize alignment of other mechanical or electrical equipment, such as by visually confirming that clamp arm (218) is gripping load cell (316). As yet another example, imaging device (318) may be used to analyze geometry of the end effector (308) or other components to determine if deformation has occurred. As yet another example, imaging device (318) may be used to identify and interpret a QR code, barcode, or other optical identifier affixed to surgical instrument (250). Optical identifiers present on a surgical instrument (250) might provide information or be used to retrieve information from a remote system. Such information could include data from a manufacturer, sterilization and use status, serial and model number data, or other such information. Other suitable ways in which imaging device (318) may be used will be apparent to those of ordinary skill in the art in view of the teachings herein. It should also be understood that imaging device (318) may be omitted from some versions.

Diagnostic and reconditioning device (270) of the present example also includes a diagnostic generator (322). Diagnostic generator (322) is configured to connect to generator connection (306) of surgical instrument (250) to provide operational power to surgical instrument (250) (e.g., to enable activation of end effector (308)). Diagnostic generator (322) is also configured to provide read and write operations to EEPROM (302) of surgical instrument (250). Diagnostic generator (322) may comprise a modified version of generator (112) with additional configurations that allow diagnostic generator (322) to function with diagnostic and reconditioning device (270). Diagnostic generator (302) may, in some versions, have at least some of the same physical hardware and device architecture as generator (112) described above; but diagnostic generator (302) may further have features and/or software that is different from a diagnostic setting that may otherwise be present on a memory of a conventional generator (112). It should also be understood that diagnostic generator (322) may be integrated with diagnostic and reconditioning device (270) into a single piece of capital equipment. Diagnostic generator (322) may additionally have sensors for determining the characteristics of power and data connections with surgical instrument (250), and may include sensors for determining voltage, current, data read speed, data write speed, and other similar characteristics.

Diagnostic generator (322) may additionally be capable of overriding one or more characteristics of surgical instrument (250). For example, if EEPROM (302) of surgical instrument (250) has been modified to deactivate surgical instrument (250) and thereby make surgical instrument (250) non-operational, diagnostic generator (322) may be configured to transmit an override signal to EEPROM (302) that will cause surgical instrument (250) to function as normal while surgical instrument (250) is attached to diagnostic generator (322). Diagnostic and reconditioning device (270) also has a processor and memory (320) so that data may be received from EEPROM (302) and sensors (314, 316, 318, 322) and stored, manipulated, transmitted, or otherwise acted upon. Processor and memory (320) additionally may be configured with instructions that may be executed to cause other components of diagnostic and reconditioning device (270) to activate or operate in a certain manner. This could include, for example, causing imaging device (318) to activate and begin to capture imaging data for end effector (308), cause diagnostic generator (322) to provide varying current levels to generator connection (306), or cause input actuator (312) to actuate activation input (304).

Diagnostic and reconditioning device (270) may also have a network device (324) allowing for wired connectivity, such as by Ethernet, universal serial bus, optical, or similar wired connections, or wireless connectivity, such as Wi-Fi, Bluetooth, radio, or similar wireless connections, that enable diagnostic and reconditioning device (270) to connect to a local area or wide area network. Network device (324) may allow diagnostic and reconditioning device (270) to communicate with a remote server (326) to provide software and configurations updates to both diagnostic and reconditioning device (270) and surgical instrument (250), analytics reporting, surgical instrument (250) registration, surgical instrument (250) feature management, and other similar operations. As another merely illustrative example, network device (324) may communicate information back to the manufacturer of surgical instrument (250), such as the number of times surgical instrument (250) has been used, other data about the way in which surgical instrument (250) has been used, data about the condition of surgical instrument (250), and/or other kind of information. As another example, information communicated by network device (324) could include product inquiries, customer complaints, safety risks, and/or other issues identified during a medical procedure in which surgical instrument (250) is used; and such information could be associated with the diagnostic profile of surgical instrument (250) and accessed via the remote server (326) to provide remote troubleshooting. As another example, information communicated by network device (324) could include terms of use agreements, warranty information, pricing information, and payment information associated with surgical instrument (250) recertification process. As another example, information communicated by network device (324) could include inventory control information, sterilization status, and cleaning status relating to surgical instrument (250).

III. Exemplary Method of Recertifying Surgical Instrument

Figure 3:
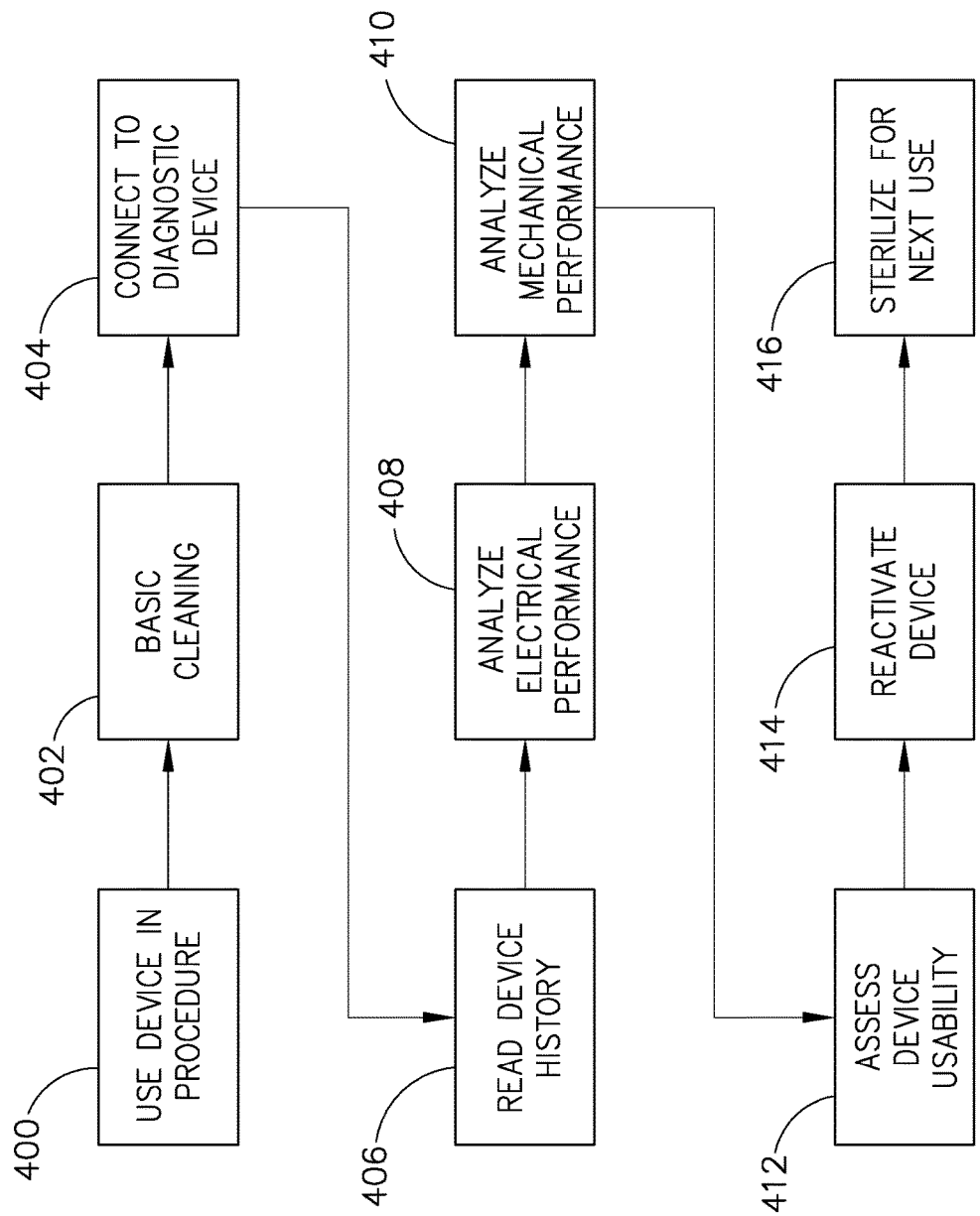
FIG. 3 depicts a flowchart of an exemplary set of high level steps that could be performed using the reconditioning device of FIG. 2 to determine the usability of the surgical instrument of FIG. 2 and recondition it for further use.

FIG. 3 shows an exemplary set of high level steps that could be performed using a device such as diagnostic and reconditioning device (270) to determine the usability of surgical instrument (250) and recondition surgical instrument (250) for further use. Surgical instrument (250) may be partially or fully deactivated upon completion of a surgical procedure (block 400) in order to prevent unlimited overuse or abuse of surgical instrument (250) by an end user. After surgical instrument (250) is used in a procedure (block 400) and fully or partially deactivated, surgical instrument (250) may need some basic cleaning (block 402) and sanitizing to remove large matter (e.g., pieces of tissue, coagulated blood, other biomaterial, etc.) and make surgical instrument (250) safe to handle and perform diagnostic testing with. Once surgical instrument (250) has been generally cleaned (block 402), surgical instrument (250) may be connected (block 404) to diagnostic and reconditioning device (270). It should be understood that the above described step of cleaning (block 402) is merely optional and may be completely omitted in some versions. It should also be understood that, in versions where a step of cleaning (block 402) is performed, the step of cleaning (block 402) may be performed manually, may be performed using an automated cleaning system, or may be performed in any other suitable fashion.

After this connection (block 404), diagnostic and reconditioning device (270) may perform diagnostics on surgical instrument (250) based upon data analysis and physical analysis of surgical instrument (250), including reading surgical instrument (250) use history (block 406), analyzing electrical performance (block 408), and analyzing mechanical performance (block 410). It should be understood that this analysis may be performed using features such as load cell (316), imaging device (318), and diagnostic generator (322), described above. Diagnostic and reconditioning device (270) may assess (block 412) the future usability of surgical instrument (250) based upon the analysis (block 408, block 410); and then one or more features or uses of surgical instrument (250) may be reactivated (block 414) to allow further use of surgical instrument (250). Once surgical instrument (250) has been reactivated (block 414), surgical instrument (250) may be disconnected from diagnostic and reconditioning device (270) and fully sterilized (block 416) by hand for use in subsequent medical procedures. It should be understood that the above described step of sterilizing (block 416) is merely optional and may be completely omitted in some versions. It should also be understood that, in versions where a step of sterilizing (block 416) is performed, the step of sterilizing (block 406) may be performed using an automated cleaning system or may be performed in any other suitable fashion.

Figure 4:
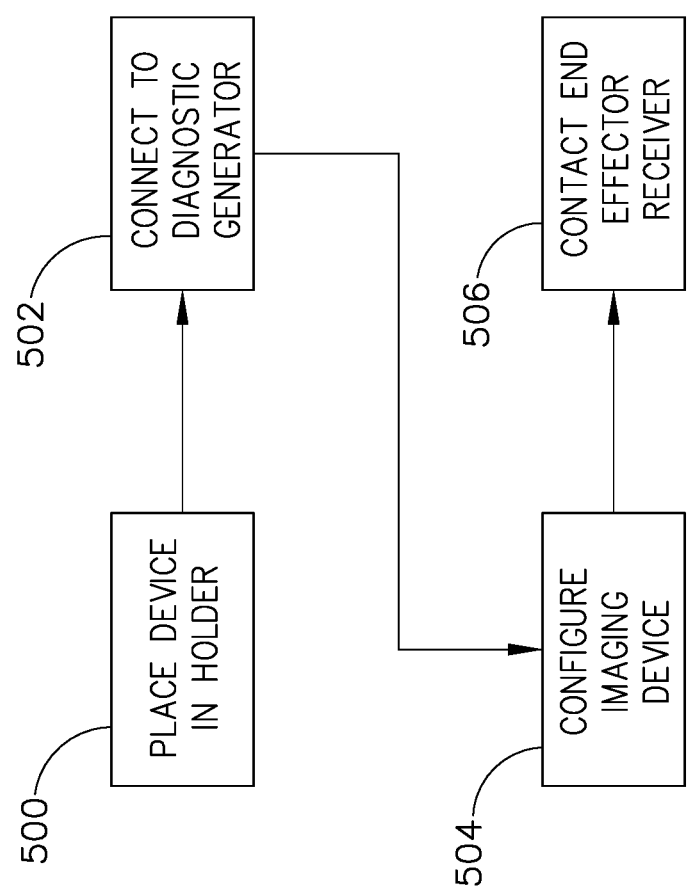
FIG. 4 depicts a flowchart of an exemplary set of steps that could be performed to connect the surgical instrument of FIG. 2 to the reconditioning device of FIG. 2.

FIG. 4 shows an exemplary set of steps that could be performed to connect a surgical instrument (250) to diagnostic and reconditioning device (270). It should be understood that the steps shown in FIG. 4 may be viewed as a set of sub-steps performed as part of the connection step (block 404) described above with reference to FIG. 3. To begin the process shown in FIG. 4, surgical instrument (250) may be first placed in a holder (block 500), such as by placing surgical device body (300) in surgical device holder (310). Surgical device holder (310) and body (300) may be configured so that proper placement is guided by physical constraints, such as where holder (310) has a shape that complements the shape of body (300), thereby causing body (300) to align and snap into place in holder (310). Placement (block 500) may also result in a placement of activation input (304) adjacent to input actuator (312) to thereby allow input actuator (312) to activate activation input (304). In addition or in the alternative, in some versions surgical instrument (250) may be activated by power or data communications transmitted via generator connection (306).

Proper placement (block 500) of surgical instrument (250) relative to diagnostic and reconditioning device (270) will also result in a connection (block 502) between generator connection (306) and diagnostic generator (322). In some versions, proper placement (block 500) of surgical instrument (250) relative to diagnostic and reconditioning device (270) will result in a connector of diagnostic generator (322) being located proximate to generator connection (306), thereby facilitating manual coupling of generator connection (306) with diagnostic generator (322) (e.g., by plugging a cable into a socket, etc.). In some other versions, proper placement (block 500) of surgical instrument (250) relative to diagnostic and reconditioning device (270) will result in automatic connection between generator connection (306) and diagnostic generator (322).

Proper placement (block 500) of surgical instrument (250) relative to diagnostic and reconditioning device (270) will also result in imaging device (318) being targeted at the components of surgical instrument (250) that will be imaged. Imaging device (318) may require additional configuration (block 504) such as fine tuning focus, lighting, or targeting movement, which may be performed manually by a user or automatically by diagnostic and reconditioning device (270). By way of example only, in versions of diagnostic and reconditioning device (270) that are capable of receiving various kinds of surgical instruments (250) (e.g., ultrasonic surgical instruments, RF electrosurgical instruments, etc.), diagnostic and reconditioning device (270) may automatically recognize the particular kind of surgical instrument (250) that is coupled with diagnostic and reconditioning device (270); and may thereby automatically configure (block 504) imaging device (318) based on the detected kind of surgical instrument (250). Various suitable ways in which such detection and configuration (block 504) may be carried out will be apparent to those of ordinary skill in the art in view of the teachings herein.

Proper placement (block 500) of surgical instrument (250) relative to diagnostic and reconditioning device (270) will also result in contact (block 506) between end effector (308) and end effector receiver (314). This contact (block 506) may occur by, for example, end effector receiver (314) being located proximate to end effector (308) to allow for manual placement of end effector (308) against end effector receiver (314). Alternatively, this contact (block 506) may result from an automatic pairing of end effector (308) with receiver (314) by a mechanical system that extends receiver (314) into place against end effector (308) as body (300) is pressed into holder (310); or an electrical system that extends receiver (314) into place based upon a user input or other input.

Once the foregoing steps (block 500, block 502, block 504, block 506) of FIG. 4 are complete, surgical instrument (250) will be in a state where surgical instrument (250) is substantially immobilized within device holder (310). Power may be supplied to surgical instrument (250) via diagnostic generator (322). EEPROM (302) may be accessed and modified via generator connection (306). Surgical instrument (250) may be activated via input actuator (312) and/or generator connection (306). End effector (308) may be imaged via imaging device (318) and/or be physically tested via end effector receiver (314), load cell (316), or both. All of these processes may be performed as part of steps (block 408, block 410) described above with reference to FIG. 3.

Figure 5:
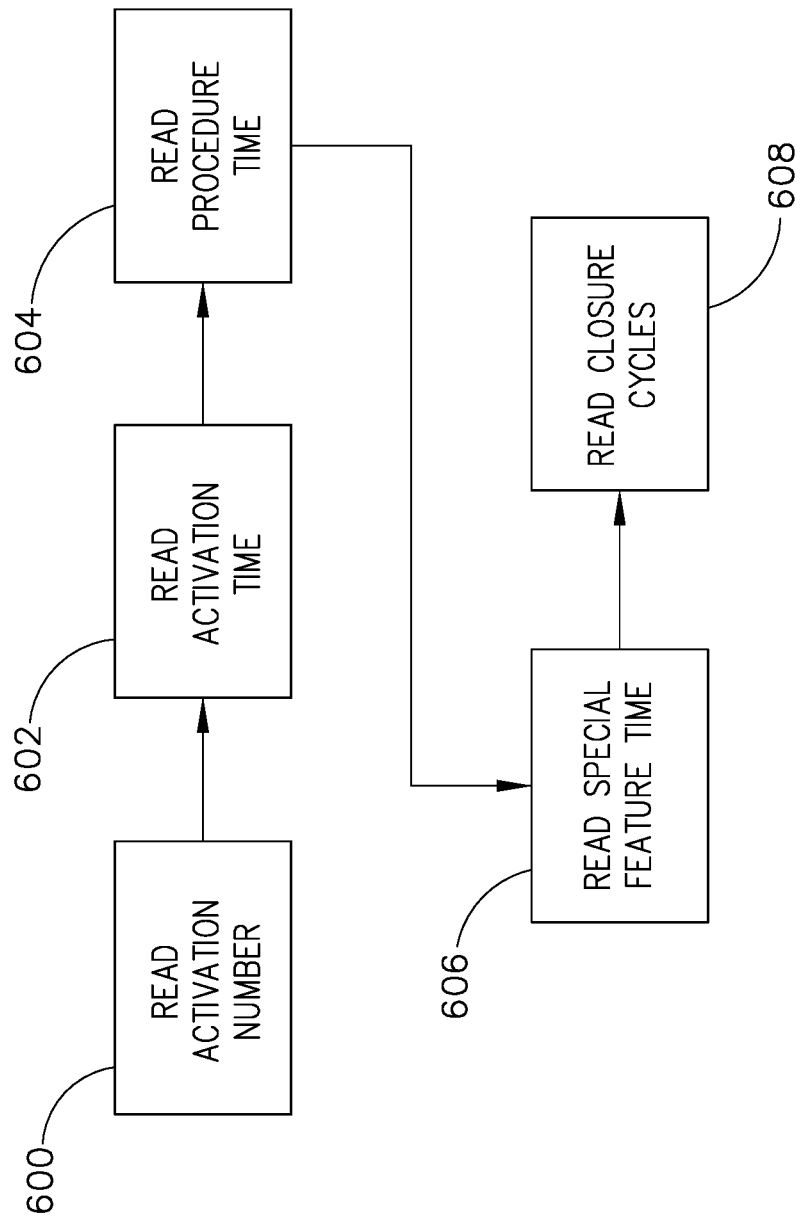
FIG. 5 depicts a flowchart of an exemplary set of steps that the reconditioning device of FIG. 2 could perform to read historic information from the surgical instrument of FIG. 2.

FIG. 5 shows an exemplary set of steps that could be performed by diagnostic and reconditioning device (270) to read historic information from surgical instrument (250). It should be understood that the steps shown in FIG. 5 may be viewed as a set of sub-steps performed as part of the reading of device history (block 406) described above with reference to FIG. 3. To begin the process shown in FIG. 5, once surgical instrument (250) is fully connected to diagnostic and reconditioning device (270), historical usage information may be pulled and analyzed from device EEPROM (302). This could include reading and compiling usage information for the number of individual times surgical instrument (250) has been activated (block 600); the total duration of time that surgical instrument (250) has been activated (block 602); the total procedure time (block 604) or total time surgical instrument (250) has been connected to a generator (112); the total duration of time that special features or special modes of surgical instrument (250) have been activated (block 606), such as adaptive tissue technology ("ATT") or other special feature modes; and the number of closure cycles (block 608), which can be used to indicate wear on clamp arm (218). As historical usage data is read from EEPROM (302) it may be processed to aggregate the data into a desired format and then stored in memory (320) or another storage medium to be used along with other factors during a final assessment of surgical instrument (250) usability (block 412).

Figure 6:
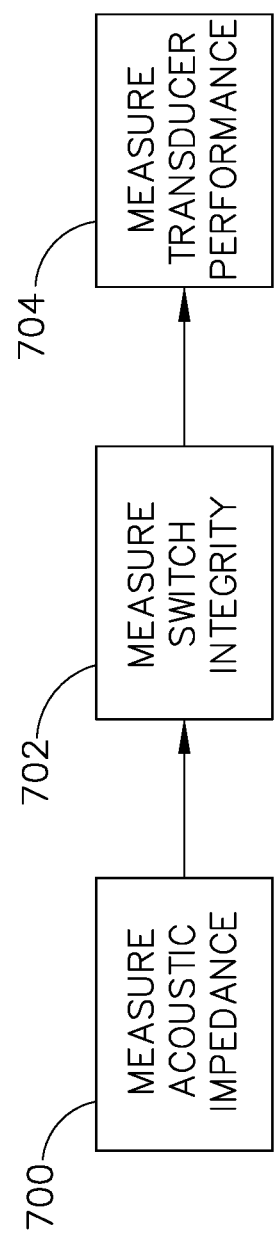
FIG. 6 depicts a flowchart of an exemplary set of steps that the reconditioning device of FIG. 2 could perform to measure electrical performance of the surgical instrument of FIG. 2.

FIG. 6 shows an exemplary set of steps that diagnostic and reconditioning device (270) may perform to measure electrical performance of surgical instrument (250). It should be understood that the steps shown in FIG. 6 may be viewed as a set of sub-steps performed as part of the electrical performance analysis step (block 408) described above with reference to FIG. 3. One characteristic of electrical performance that may be measured is acoustic impedance (block 700) of end effector (308), where end effector (308) includes an ultrasonic blade (216). Various suitable ways in which acoustic impedance may be measured (block 700) will be apparent to those of ordinary skill in the art in view of the teachings herein. By way of example only, measuring acoustic impedance (block 700) may be accomplished via one or more acoustic impedance sensors located on diagnostic and reconditioning device (270), such as at end effector receiver (314), surgical device holder (310), diagnostic generator (322), and/or any other location that may be suitable for an acoustic impedance sensor. Input actuator (312) may be activated to activate the acoustic drivetrain of surgical instrument (250) while end effector receiver (314) is moved into varying levels of contact with end effector (308), in order to simulate the desired contact, so that the acoustic impedance sensors can gather data. It will be understood that, if the acoustic impedance is outside of an acceptable range, this may indicate that end effector (308) and/or one or more of its mechanical or electrical connectors is/are physically damaged.

Another characteristic of electrical performance that may be measured is switch integrity (block 702). Switch integrity might decrease as a result of usage of surgical instrument (250), and may result in interference or loss of transmission of electrical signals along the circuitry of surgical instrument (250). For example, activation input (304) may appear undamaged based upon casual visual observation, but circuitry contained in surgical device body (300) that is connected or activated by the actuation of activation input (304) may degrade due to the stresses of using surgical instrument (250) in a surgical procedure, cleaning, sanitizing, or otherwise. As circuitry degrades, the signal that is created or transmitted as a result of the actuation of activation input (304) may become unstable or may cease altogether. Diagnostic generator (322) may contain one or more sensors that receive and analyze signals that are created as a result of actuation of activation input (304) and/or other switches of the surgical device being actuated. Input actuator (312) may be activated to cause surgical instrument (250) to perform one or more features such as activating an ultrasonic blade (216), activating RF electrodes, cutting, clamping, etc., so that data may be gathered by the sensor.

Another characteristic of electrical performance that may be measured is transducer performance (block 704) for versions of surgical instrument (250) that have integrated transducers (e.g., like transducer assembly (210)). Diagnostic generator (322) may contain one or more sensors that can detect the power consumption and output of surgical instrument (250) during use. Input actuator (312) can be activated to cause the surgical instrument (250) to perform one or more features that utilize transducer assembly (210) and resulting metrics can be measured (704). Metrics measured by the sensors could include capacitance, power consumption, and phase margin. The transducer performance measurements (block 704), along with the switch integrity (block 702) and acoustic impedance (block 700) may then be preserved in a memory (320) or other storage medium and used during a device usability assessment step (block 412).

Figure 7:
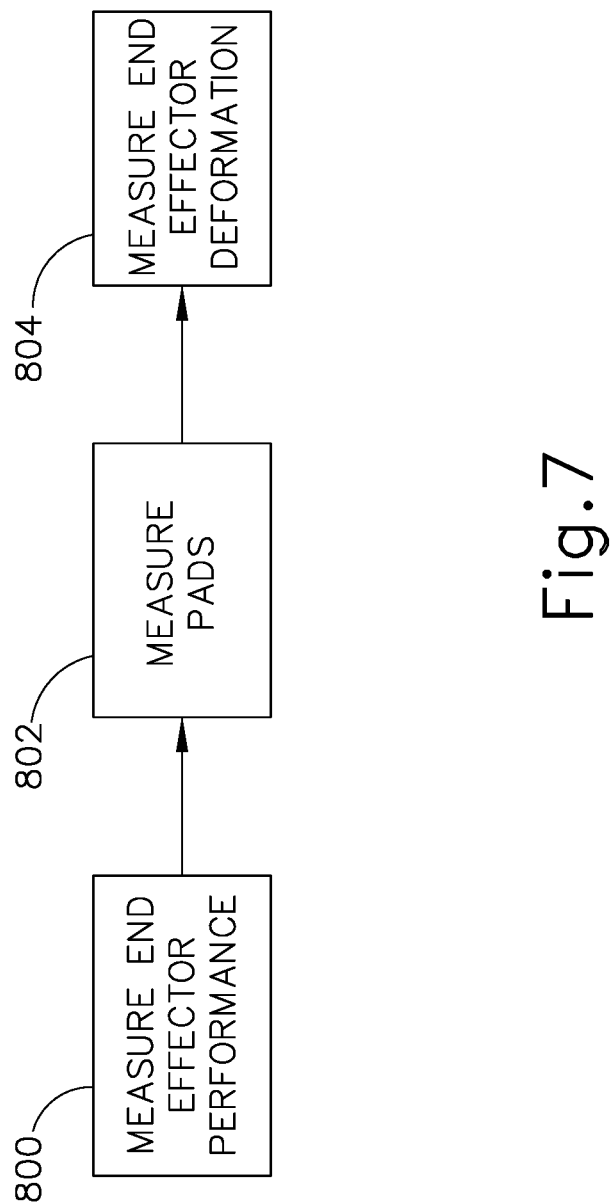
FIG. 7 depicts a flowchart of an exemplary set of steps that the reconditioning device of FIG. 2 could perform to measure mechanical performance of the surgical instrument of FIG. 2.

FIG. 7 shows an exemplary set of steps that could be performed by diagnostic and reconditioning device (270) to measure mechanical performance of surgical instrument (250). It should be understood that the steps shown in FIG. 7 may be viewed as a set of sub-steps performed as part of the mechanical performance analysis step (block 410) described above with reference to FIG. 3. To begin the process shown in FIG. 7, one characteristic of mechanical performance that may be measured is end effector performance (block 800). This could include measuring characteristics such as the grip or clamp force of clamp arm (218) as measured by load cell (316). Measuring end effector performance (block 800) could also include measuring cutting force, cauterizing temperature, ultrasonic effector frequency, and/or other end effector (308) performance characteristics. One or more sensors placed in the end effector receiver (314) or load cell (316) may be configured to measure such characteristics while surgical instrument (250) is activated by input actuator (312).

In versions where surgical instrument (250) includes a clamp arm (e.g., like clamp arm (218)) having a clamp pad, another mechanical characteristic that may be measured is pad dimensions (block 802). For instance, in versions of surgical instrument (250) having a clamp pad that is formed of polytetrafluoroethylene (PTFE) and/or some other kind of relatively soft material, the material forming the clamp pad may tend to degrade during use of surgical instrument (250) in a surgical procedure. Various suitable ways in which the characteristics of a used clamp pad may be measured (block 802) will be apparent to those of ordinary skill in the art in view of the teachings herein. By way of example only, the thickness and/or other dimensions of the clamp pad may be visually observed by imaging device (318) to generate image data that may be examined to estimate remaining pad or surface depth; or to compare to image data from newly manufactured clamp pads or surfaces. While the present example includes measuring dimensions (block 802) of a clamp pad, it should be understood that similar measurements may be made for other components or features of surgical instrument (250) (e.g., coatings, etc.) that may tend to degrade during use of surgical instrument (250) in a surgical procedure.

Another mechanical characteristic that may be measured is end effector deformation (block 804). It should be understood that some versions of end effector (308) may tend to deform due to repeated use during a surgical procedure, and such deformation may have an adverse impact on performance of end effector (308). For instance, a clamp arm (218) or blade (216) may warp, or the pivotal coupling of clamp arm (218) to shaft assembly (212) may deform, resulting in misalignment between clamp arm (218) and blade (216) and/or otherwise resulting in an unacceptable closure profile of clamp arm (218) relative to blade (216). Various suitable ways in which end effector deformation may be measured (block 804) will be apparent to those of ordinary skill in the art in view of the teachings herein. By way of example only, imaging device (318) may capture images of end effector (308) from one or more positions. In some such versions, imaging device (318) may be mounted on a movable element that can be extended, retracted, rotated, or otherwise mechanically moved so that end effector (308) may be imaged from different positions. In addition or in the alternative, imaging device (318) may remain stationary, while surgical device holder (310) manipulates the position of surgical instrument (250) itself to allow for the capture images from multiple positions. In still other versions, imaging of end effector (308) may be performed from only a single position; or may be performed from a single position by a three dimensional capable imaging device (318).

Image data generated from imaging of end effector (308) may be used to compare to newly manufactured examples in order to determine deformation caused by use or abuse; or may be used to generate virtual models of end effector (308) that may be compared to virtual models of end effectors that are in an ideal or allowable physical state. Measured end effector performance (block 800), pad quality (block 802), and end effector deformation (block 804) may be retained on a memory (320) or other storage medium and used during a device usability assessment step (block 412).

Figure 8:
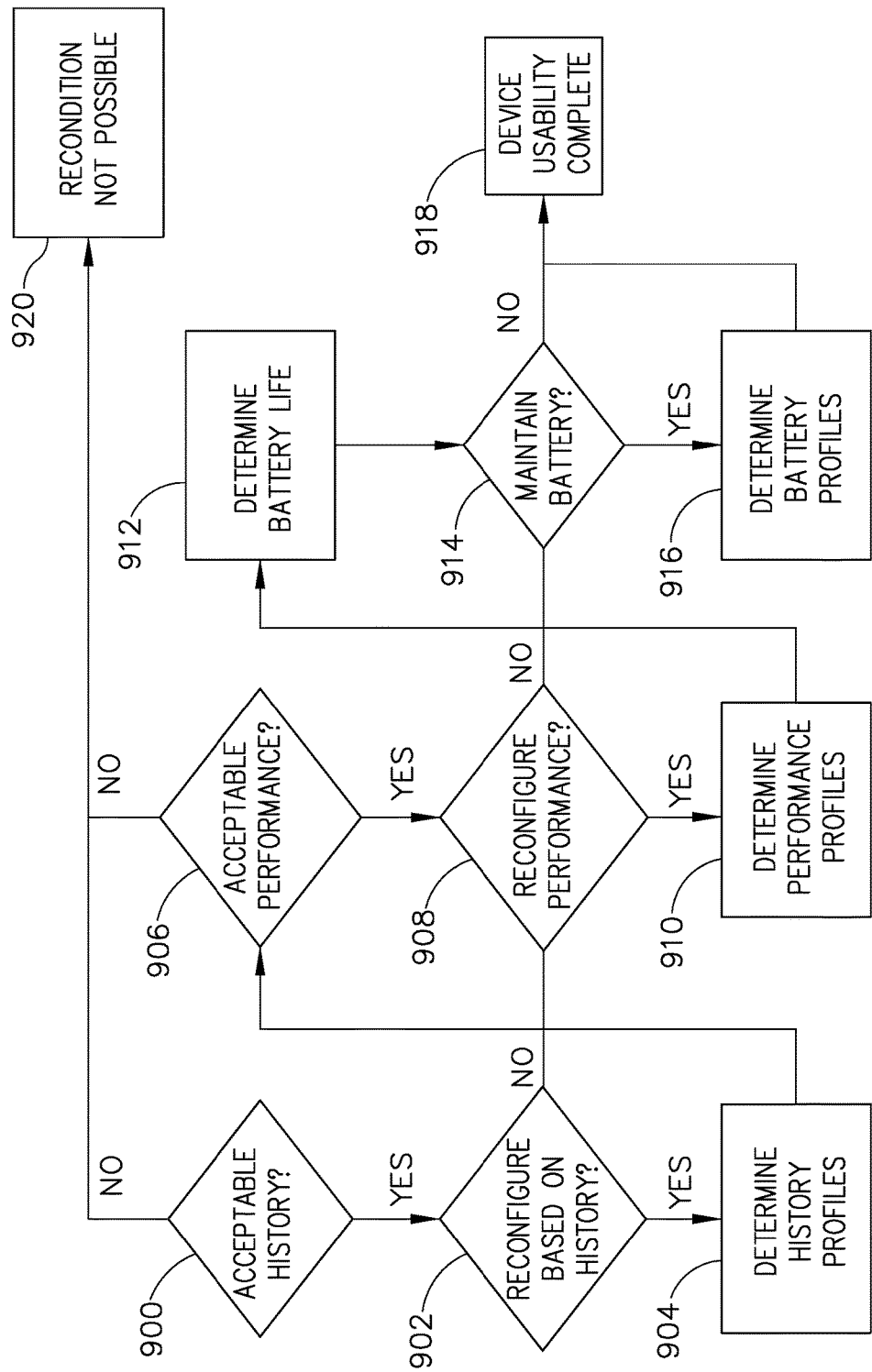
FIG. 8 depicts a flowchart of an exemplary set of steps that the reconditioning device of FIG. 2 could perform to assess usability of the surgical instrument of FIG. 2.

FIG. 8 shows an exemplary set of steps that diagnostic and reconditioning device (270) could perform to assess usability of surgical instrument (250). It should be understood that the steps shown in FIG. 8 may be viewed as a set of sub-steps performed as part of the device usability assessment step (block 412) described above with reference to FIG. 3. Once suitable information and metrics are available (block 406, block 408, block 410), a determination can be made about the current physical state of surgical instrument (250) and whether the state of surgical instrument (250) allows for surgical instrument (250) to be reconditioned and partially or fully reactivated.

The process shown in FIG. 8 may begin with a determination (block 900) of whether the usage history (block 406) is acceptable enough to provide safe reconditioning of surgical instrument (250) for further use. If it is determined that surgical instrument (250) may not be safely used or reconditioned based upon usage history (block 900), diagnostic and reconditioning device (270) will report that reconditioning of surgical instrument (250) is not possible (block 920). For example, if an ultrasonic surgical instrument (200) has been used beyond its normal life by a user, perhaps by keeping the ultrasonic surgical instrument (200) disconnected from a generator (112) except for very brief periods when ultrasonic surgical instrument (200) is being actively used to cut tissue, in order to prevent a device lockout based upon total time connected to a generator (112), the device usage history may indicate over six hours of activation time. If such an ultrasonic surgical instrument (200) has only been tested or certified for safe use of up to three hours of activation time, it may be determined that the device usage history is unacceptable (block 900); and that reconditioning is therefore not possible (block 920). Other scenarios in which the usage history of a surgical instrument (250) may indicate that reconditioning is not possible (block 920) (or is otherwise not acceptable) will be apparent to those of ordinary skill in the art in view of the teachings herein.

If it is instead determined that surgical instrument (250) has an acceptable usage history (block 900), such as where an ultrasonic surgical instrument (200) has only been activated for one hour total and safety testing indicates that ultrasonic surgical instrument (200) would have a safe use life of three hours, a determination will be made if any reconfigurations are necessary based on the device usage history (block 902). Reconfigurations that may be necessary might include, for example, adjusting error thresholds for a surgical instrument (250) in response to extensive previous use so that surgical instrument (250) is more or less likely to report an error during use; adjusting the maximum operational output of surgical instrument (250) based upon high previous use; or similar reconfigurations.

If is determined that there may be some necessary or optional reconfigurations (block 902), these reconfigurations will be organized into one or more history profiles (block 904) that individually describe changes that must be made or may selectively be made to surgical instrument (250) to allow for varying types of future use. For example, one history profile may be a reconfiguration necessitated by a high previous usage of surgical instrument (250). Another history profile may be an optional reconfiguration that will result in the re-activation of a particular optional feature of surgical instrument (250). For example, if an ultrasonic surgical instrument (200) has a special feature such as ATT, this special feature may be disabled after a small amount of usage due to the additional stress placed on ultrasonic surgical instrument (200) by the use of the special feature. Based upon device usage, this feature may optionally be re-enabled but is not a necessity. Once history profiles have been determined (block 904), whether optional or necessary, or if there are no reconfigurations based upon history that are identified (block 902), device usability assessment based upon device use history is complete.

Next, a determination of device usability based upon device performance (block 906) may be made to determine if the current mechanical and electrical condition and performance of surgical instrument (250) will allow for safe further use of the device. If it is determined that the performance of surgical instrument (250) is outside acceptable levels for reconditioning, diagnostic and reconditioning device (270) will report that reconditioning is not possible (block 920). This could occur where, for example, current acoustic impedance, switch integrity, transducer performance, end effector performance, pad quality, or end effector deformation fall outside of an acceptable range indicating that surgical instrument (250) cannot be safely used and that no configuration change is possible that will result in surgical instrument (250) being safe to use. If the performance characteristics of surgical instrument (250) fall within an acceptable range (block 906), it will be determined if any necessary or optional reconfigurations are needed or possible (block 908). This could include adjusting one or more configurations stored on EEPROM (302) to account for the changed physical characteristics of surgical instrument (250) since surgical instrument (250) was first manufactured and configured.

For example, in the context of ultrasonic surgical instrument (200), if it is determined that the clamp pad of clamp arm (218) is at 50% thickness, the maximum clamp strength or maximum clamp travel distance of clamp arm (218) may be reconfigured to allow for additional use of surgical instrument (200) while accounting for the reduced clamp pad thickness. As another example, if it determined that switch integrity has degraded, surgical instrument (250) may be reconfigured so that surgical instrument (250) can be activated by an alternate switch, such as a foot switch, instead of by activation input (304). As another example, if capacitance, power consumption, and/or phase margin has changed since manufacture, the voltage and current drawn by surgical instrument (250) may be reconfigured to bring capacitance, power consumption, and/or phase margin back to original metrics. Further examples of reconfigurations to account for changes in mechanical or electrical performance exist and will be apparent to one of ordinary skill in the art in light of the disclosure herein.

Once the necessary and optional reconfigurations have been determined and organized into performance profiles (block 910), diagnostic and reconditioning device (270) may assess battery characteristics (block 912) if surgical instrument (250) includes a battery. This could include an internal battery or an externally removable battery, which in some versions of surgical instrument (250) may provide power to surgical instrument (250) in addition to or in the alternative to a generator (112) providing power to surgical instrument (250). When determining battery life (block 912), diagnostic and reconditioning device (270) may determine the battery's current charge, may attempt to charge the battery, may determine the rate at which the battery is able to be charged, and may perform additional testing of the battery. If the battery needs to be reconfigured or maintained (block 914), diagnostic and reconditioning device (270) may determine battery profiles that may include necessary or optional changes such as reconfiguring the voltage or current drawn from the battery, reconfiguring the battery charge rate, reconfiguring the battery maximum charge level, suggesting replacement of the battery, or other similar changes. If there is no battery present, or if the battery is fully charged and exhibits no errors or needed reconfigurations, the device usability assessment is complete (block 918).

Figure 9:
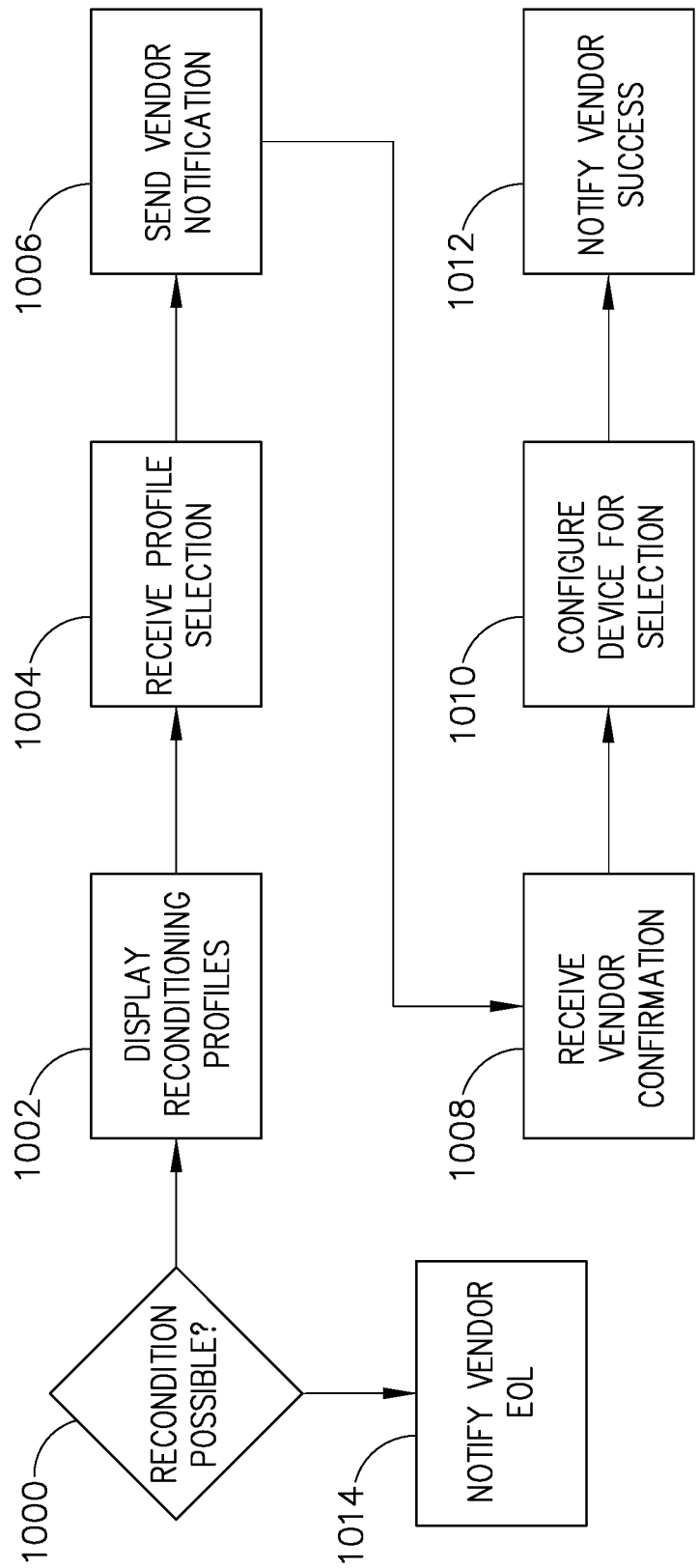
FIG. 9 depicts a flowchart of an exemplary set of steps that the reconditioning device of FIG. 2 could perform to reactivate and recondition the surgical instrument of FIG. 2 for safe use.

FIG. 9 shows an exemplary set of steps that diagnostic and reconditioning device (270) could perform to reactivate and recondition surgical instrument (250) for safe use. If a device usability assessment (block 412) determines that surgical instrument (250) may not be reconditioned and reactivated (block 1000), the user and vendor may be notified (block 1014) that surgical instrument (250) has reached an end of life state where reconditioning is not possible or acceptable. A user may be notified via a display on diagnostic and reconditioning device (270) and/or via a display on surgical instrument (250), indicating that surgical instrument (250) has no remaining life and that surgical instrument (250) should be discarded or returned to the manufacturer. The hospital in which surgical instrument (250) is located may also be notified that surgical instrument (250) is no longer usable. For instance, this notification may be transmitted to a hospital's inventory management system via network device (324), such that the hospital's inventory management system may then coordinate replacement of the spent surgical instrument (250). The manufacturer or vendor may also be notified by, for example, a notification transmitted via network device (324) to a remote server (326) so that the vendor may update their surgical instrument (250) registration records or initiate contact with the user to arrange for the delivery of a replacement surgical instrument (250). The notification may include additional information and analytics generated during the diagnostic and reconditioning process, including, for example, surgical instrument (250) usage, mechanical performance, electrical performance, various reconfiguration profiles determined for surgical instrument (250), and information indicating why surgical instrument (250) is not able to be reconditioned.

If the usability assessment (block 412) indicates that surgical instrument (250) is reusable, diagnostic and reconditioning device (270) will display one or more reconditioning profiles (block 1002) to the user. Reconditioning profiles (block 1002) may include a list of all the necessary and optional reconfigurations (block 904, block 910, block 916) determined for surgical instrument (250) during the usability assessment (block 412). Reconditioning profiles could include, for example, reactivating surgical instrument (250) to different levels of functionality, such as enabling all of the original features of surgical instrument (250); only enabling the primary feature of surgical instrument (250); modifying the functionality of triggers, switches, or other inputs of surgical instrument (250); modifying current set points for power supply to surgical instrument (250); modifying ATT set points; limiting motor output in order to limit speed or power of surgical instrument (250); or other similar reconfigurations.

The displayed reconditioning (block 1002) profiles may be bundled together to show the different levels to which surgical instrument (250) may be reconditioned. For example, a minimal reconditioning profile may include all necessary reconfiguration profiles that must be applied to place surgical instrument (250) in a minimal state of usability, but may not include optional reconfigurations such as reactivating special features such as ATT. An optional reconditioning profile may include all the necessary reconfiguration profiles, as well as one or more optional reconfiguration profiles that will place surgical instrument (250) in a state of usability that includes non-core features or special features. Essentially, the user may be presented with several options, one or more of which may be selected, and with varying selections resulting surgical instrument (250) being either partially reactivated for subsequent use, or fully reactivated for subsequent use. Each option may be further presented along with conditions or requirements for selecting the option, which may include contractual limitations on the use of the reconditioned surgical instrument (250), limitations on liability related to use of the reconditioned surgical instrument (250), and pricing options or plans related to completing reconditioning of the surgical instrument (250).

After displaying the profiles, diagnostic and reconditioning device (270) may receive (block 1004) a user selection of one or more usability profiles indicating the level of usability that surgical instrument (250) should be reconditioned to. A notification may be sent to the vendor (block 1006) or manufacturer via network device (324) notifying the vendor of the selected reconditioning profile. Vendor approval of the reconditioning may occur manually or automatically, and a transmitted approval will be received (block 1008) by diagnostic and reconditioning device (270) via network device (324). After the vendor confirmation is received (block 1008), the selected reconditioning profile will be applied (block 1010) to surgical instrument (250) by modifying the contents of EEPROM (302) via the data connection of diagnostic generator (322) so that the configuration of surgical instrument (250) may be permanently changed. Applying the reconditioning profile (block 1010) to surgical instrument (250) may also include modifying the contents of EEPROM (302) to partially or fully reactivate surgical instrument (250) for subsequent procedures; and may also include modifying the device usage history on EEPROM (302) to prevent premature deactivation of surgical instrument (250) upon subsequent uses.

Once the reconditioning profile has been successfully applied (block 1010) to surgical instrument (250), diagnostic and reconditioning device (270) may test various capabilities of surgical instrument (250) using input actuator (312), end effector receiver (314), load cell (316), and/or imaging device (318) to verify that the configuration was successful and that surgical instrument (250) is safe to use for subsequent procedures; and the notify the vendor (block 1012) of the successful reconditioning so that the vendor may update their device registration records, generate invoices or other correspondence, and/or take other actions. The user may at this point send surgical instrument (250) to another station for further cleaning and sterilization of surgical instrument (250), thereby completing the processes needed to enable surgical instrument (250) to be used in a surgical procedure.

Management of deactivation and reactivation of surgical instruments (250) may be implemented in varying ways in order to prevent reactivation of surgical instrument (250) in a manner not intended by the manufacturer or vendor. For example, in some versions a physical or electrical switch may be actuated in order to switch surgical instrument (250) from a state of disabled functionality to a state of enabled functionality. While a simple approach, this approach may also be circumvented or abused by an end user that is able to bypass diagnostic and reconditioning device (270) and directly interact with the physical or electrical switch. In some versions, surgical instrument (250) may be configured with an encrypted reactivation key or authentication requirement that would prevent reactivation attempts that could not supply a matching key or authentication requirement. A diagnostic and reconditioning device (270) or generator (112) could be configured with a set of reactivation keys or other data needed to match the reactivation key or authentication. Such an approach may reduce the likelihood that a surgical instrument (250) could be reactivated by direct manipulation. Reactivation keys on a generator (112) or diagnostic and reconditioning device (270) could be refreshed from time to time as software updates are received from a connected storage such as a USB drive; or from an internet connection for internet connected devices.

While the above examples include the diagnostic functionality (e.g., the steps shown in FIGS. 4-8) and the reconditioning functionality (e.g., the steps shown in FIG. 9) all being carried out by the same single diagnostic and reconditioning device (270), it should be understood that some versions may provide such functionality in two separate devices. For instance, a diagnostic device may provide the diagnostic functionality described above; while a separate reconditioning device may provide the reconditioning functionality described above. Other suitable arrangements and configurations of hardware that may be used to perform the methods described herein will be apparent to those of ordinary skill in the art in view of the teachings herein.

While the teachings herein have been provided mainly in the context of an ultrasonic surgical instrument (250), it should be understood that the teachings herein may also be readily applied to various other kinds of instruments. By way of example only, the teachings herein may be readily applied in contexts where ultrasonic surgical instrument (250) is replaced with an instrument that provides combined ultrasonic and electrosurgical capabilities. Examples of such a combined ultrasonic and electrosurgical instrument are described in U.S. Pub. No. 2015/0141981, now U.S. Pat. No. 9,949,785, issued Apr. 24, 2018 and U.S. Pat. No. 8,663,220, the disclosures of which are incorporated by reference herein. It should therefore be understood that variations of diagnostic and reconditioning device (270), and variations of the associated methods described herein, may be used with combined ultrasonic and electrosurgical instruments.

By way of further example only, the teachings herein may be readily applied in contexts where ultrasonic surgical instrument (250) is replaced with an instrument that provides electrosurgical capabilities without also providing ultrasonic capabilities. An example of such an electrosurgical instrument is the ENSEAL® electrosurgical instrument by Ethicon Endo-Surgery, Inc. of Cincinnati, Ohio. Further examples of electrosurgical instruments are described in U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein. It should therefore be understood that variations of diagnostic and reconditioning device (270), and variations of the associated methods described herein, may be used with electrosurgical instruments.

By way of further example only, the teachings herein may be readily applied in contexts where ultrasonic surgical instrument (250) is replaced with a surgical stapling instrument. An example of such a surgical stapling instrument is the ECHELON® stapling instrument by Ethicon Endo-Surgery, Inc. of Cincinnati, Ohio. Further examples of surgical stapling instruments are described in U.S. Pub. No. 2015/0272575, entitled "Surgical Instrument Comprising a Sensor System," published Oct. 1, 2015, now U.S. Pat. No. 9,913,642, issued Mar. 13, 2018, the disclosure of which is incorporated by reference herein. It should therefore be understood that variations of diagnostic and reconditioning device (270), and variations of the associated methods described herein, may be used with surgical stapling instruments.

Still other suitable instruments that may be used with diagnostic and reconditioning device (270) and the associated methods described herein, including variations of reconditioning device (270) and variations of the associated methods described herein, will be apparent to those of ordinary skill in the art.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A system comprising: (a) a generator configured to be coupled with a generator connection of a used surgical instrument, wherein the generator is configured to: (i) provide power to the used surgical instrument, (ii) receive data from the used surgical instrument, and (iii) transmit data to the used surgical instrument; (b) a surgical instrument actuator configured to cause the used surgical instrument to activate one or more of a set of surgical instrument modes; (c) a memory, wherein the memory is configured to store a set of instructions; and (d) a processor, wherein the processor is configured to execute the instructions to: (i) receive a set of usage data from the used surgical instrument, (ii) cause the input actuator to activate the used surgical instrument in a first mode, (iii) while the first mode is active, measure a set of electrical characteristics of the used surgical instrument, (iv) based upon the set of usage data and the set of electrical characteristics, create a reconditioning profile that may be applied to the used surgical instrument.

EXAMPLE 2

The system of Example 1, further comprising an imaging device positioned to capture an image of an end effector of the used surgical instrument, wherein the processor is further configured to execute instructions to: (i) capture a set of image data for the end effector via the imaging device, and (ii) based upon the set of usage data, the set of electrical characteristics, and the set of image data, create a reconditioning profile that may be applied to the used surgical instrument.

EXAMPLE 3

The system of Example 2, wherein the set of image data comprises one or more images of a feature of the used surgical instrument, and wherein the processor is further configured to: (i) when a thickness of the feature meets a safety threshold, determine the reconditioning profile, (ii) when the thickness of the feature falls short of the safety threshold by a first measurement value, determine the reconditioning profile and include in the reconditioning profile a surgical instrument reconfiguration that allows the thickness of the feature to meet the safety threshold, and (iii) when the thickness of the feature falls short of the safety threshold by a second measurement value, not create the reconditioning profile, wherein the second measurement value is greater than the first measurement value.

EXAMPLE 4

The system of any one or more of Examples 2 through 3, wherein the configuration to create a reconditioning profile further comprises instructions that may be executed by the processor to compare the set of image data to a set of new device image data and determine a level of deformity of the end effector of used surgical instrument.

EXAMPLE 5

The system of any one or more of Examples 1 through 4, further comprising a load cell configured to receive the end effector, wherein the configuration to create a reconditioning profile further comprises instructions that may be executed by the processor to cause: (i) an end effector of the surgical instrument to activate and apply a force to the load cell, and (ii) the load cell to measure the force.

EXAMPLE 6

The system of any one or more of Examples 1 through 5, wherein the surgical instrument actuator is configured to physically actuate a user input of the used surgical instrument.

EXAMPLE 7

The system of any one or more of Examples 1 through 6, wherein the surgical instrument actuator is configured to transmit a signal to the used surgical instrument.

EXAMPLE 8

The system of any one or more of Examples 1 through 7, further comprising a display, wherein display is configured to display the reconditioning profile, and wherein the processor is further configured to receive a user selection indicating that the reconditioning profile should be applied to the used surgical instrument.

EXAMPLE 9

The system of Example 8, further comprising a network device in communication with a remote server, wherein the network device is configured to transmit the user selection to the remote server, and wherein the network device is further configured to transmit a notification to the remote server when one or more of the set of surgical instrument modes are enabled.

EXAMPLE 10

The system of any one or more of Examples 1 through 9, wherein the set of usage data comprises one or more of (A) a surgical instrument activation count associated with the used surgical instrument, (B) a surgical instrument activation duration count associated with the used surgical instrument, (C) a surgical instrument generator connection duration count associated with the used surgical instrument, or (D) a surgical instrument close cycle count associated with the used surgical instrument; and wherein the set of electrical characteristics comprises one or more of (A) capacitance associated with the used surgical instrument, (B) power consumption associated with the used surgical instrument, or (C) phase margin associated with the used surgical instrument.

EXAMPLE 11

The system of any one or more of Examples 1 through 10, wherein the reconditioning profile comprises: (A) a surgical instrument reconfiguration, wherein the surgical instrument reconfiguration is configured to be written to a memory of the used surgical instrument to modify operation of the used surgical instrument, and (B) a surgical instrument activation dataset, wherein the surgical instrument activation dataset is configured to be written to the memory of the used surgical instrument to enable one or more of the set of surgical instrument modes.

EXAMPLE 12

A method comprising: (a) at a reconditioning device, reading a set of usage data from a used surgical instrument; (b) activating one or more of a set of surgical instrument modes of the used surgical instrument via an input actuator of the reconditioning device and measuring a set of electrical characteristics of the used surgical instrument; (c) measuring a set of mechanical characteristics of the used surgical instrument via the reconditioning device; (d) creating, based upon the set of usage data, the set of electrical characteristics, and the set of mechanical characteristics, a reconditioning profile that may be applied to the used surgical instrument by the reconditioning device; (e) receiving a user input indicating that the reconditioning profile should be applied to the used surgical instrument; and (f) applying the reconditioning profile to the used surgical instrument in response to the user input, wherein applying the reconditioning profile to the used surgical instrument enables one or more of the set of surgical instrument modes.

EXAMPLE 13

The method of Example 12, wherein the step of measuring the set of electrical characteristics of the used surgical instrument comprises one or more of the following acts: (i) measuring acoustic impedance of an ultrasonic blade of the used surgical instrument, (ii) measuring the conductivity of an activation circuit of the used surgical instrument, or (iii) measuring at least one of capacitance, power consumption, or phase shift margin of a transducer of the used surgical instrument.

EXAMPLE 14

The method of any one or more of Examples 12 through 13, wherein the reconditioning profile comprises a surgical instrument reconfiguration, the method further comprising writing the surgical instrument reconfiguration to a memory of the used surgical instrument to modify the electrical characteristics of the used surgical instrument during activation.

EXAMPLE 15

The method of any one or more of Examples 12 through 14, wherein the step of measuring the set of mechanical characteristics of the used surgical instrument comprises one or more of the following acts: (i) measuring force applied by an end effector of the used surgical instrument to a load cell of the reconditioning device, (ii) measuring thickness of a clamp pad of the end effector with an imaging device of the reconditioning device, or (iii) measuring deformity of the end effector with an imaging device of the reconditioning device.

EXAMPLE 16

The method of Example 15, further comprising the steps of, if the force applied by the end effector the load cell does not fall between a minimum force threshold and a maximum force threshold: (a) terminating the creation of the reconditioning profile; and (b) indicating to a user that reconditioning of the surgical instrument is not possible.

EXAMPLE 17

The method of any one or more of Examples 15 through 16, further comprising the steps of, if the thickness of the clamp pad of the end effector does not fall between a minimum thickness threshold and a maximum thickness threshold: (a) terminating the creation of the reconditioning profile; and (b) indicating to a user that reconditioning of the surgical instrument is not possible.

EXAMPLE 18

The method of any one or more of Examples 15 through 17, further comprising the steps of, if the end effector displays unsafe deformity relative to a new end effector: (a) terminating the creation of the reconditioning profile; and (b) indicating to a user that reconditioning of the surgical instrument is not possible.

EXAMPLE 19

The method of any one or more of Examples 12 through 18, further comprising the steps: (a) displaying the reconditioning profile to a user via a display of the reconditioning device; (b) displaying a set of conditions to the user via the display, the set of conditions indicating a cost associated with applying the reconditioning profile to the used surgical instrument; and (c) after receiving the user input indicating that the reconditioning profile should be applied to the used surgical instrument, sending a purchase signal to a remote server via a network device of the reconditioning device identifying the user, the used surgical instrument, and the reconditioning profile.

EXAMPLE 20

A system comprising: (a) a used surgical instrument comprising: (i) an activation input, (ii) an end effector, the end effector comprising an ultrasonic blade and a clamp arm, the clamp having a clamp pad, (iii) a generator connection, and (iv) a surgical instrument body, and (b) a reconditioning device comprising: (i) a surgical instrument holder, wherein the surgical instrument holder is configured to hold the surgical instrument body, (ii) a generator configured to couple with the generator connection, wherein the generator is configured to: (A) provide power to the used surgical instrument, (B) receive data from the used surgical instrument, and (C) transmit data to the used surgical instrument, (iii) a surgical instrument actuator configured to actuate the activation input and thereby activate the end effector, (iv) an imaging device positioned to capture an image of the end effector, (v) a load cell configured to receive and measure a clamping force of the clamp arm, and (vi) a memory, wherein the memory is configured to store a set of instructions, and (vii) a processor, wherein the processor is configured to execute the instructions to: (A) receive a set of usage data from the used surgical instrument, (B) cause the input actuator to activate the used surgical instrument in a first mode, (C) while the first mode is active, measure a set of electrical characteristics of the used surgical instrument, (D) based upon the set of usage data, the set of electrical characteristics, end effector structural characteristics as visualized by the imaging device, and the clamping force, create a reconditioning profile that may be applied to the used surgical instrument, (E) apply the reconditioning profile to the used surgical instrument, thereby enabling at least one operational mode of the used surgical instrument.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A system comprising:
   (a) a generator configured to be coupled with a generator connection of a used surgical instrument, wherein the generator is configured to:
      (i) provide power to the used surgical instrument,
      (ii) receive data from the used surgical instrument, and
      (iii) transmit data to the used surgical instrument;
   (b) a surgical instrument actuator configured to, during a post-procedure reconditioning process, physically actuate an instrument trigger of the used surgical instrument and thereby cause the used surgical instrument to activate one or more of a set of surgical instrument modes;
   (c) a memory, wherein the memory is configured to store a set of instructions; and
   (d) a processor, wherein the processor is configured to, during the post-procedure reconditioning process, execute the instructions to:
      (i) receive a set of usage data from the used surgical instrument,
      (ii) cause the surgical instrument actuator to activate the used surgical instrument in a first mode,
      (iii) while the first mode is active, measure a set of electrical characteristics of the used surgical instrument, and
      (iv) based upon the set of usage data and the set of electrical characteristics, create a reconditioning profile that may be applied to the used surgical instrument.

2. The system of claim 1, further comprising an imaging device positioned to capture an image of an end effector of the used surgical instrument, wherein the processor is further configured to, during the post-procedure reconditioning process, execute instructions to:
   (i) capture a set of image data for the end effector via the imaging device, and
   (ii) based upon the set of usage data, the set of electrical characteristics, and the set of image data, create a reconditioning profile that may be applied to the used surgical instrument.

3. The system of claim 2, wherein the set of image data comprises one or more images of a feature of the used surgical instrument that are captured during the post-procedure reconditioning process, and wherein the processor is further configured to:
   (i) when a thickness of the feature meets a safety threshold, determine the reconditioning profile,
   (ii) when the thickness of the feature falls short of the safety threshold by a first measurement value, determine the reconditioning profile and include in the reconditioning profile a surgical instrument reconfiguration that allows the thickness of the feature to meet the safety threshold, and
   (iii) when the thickness of the feature falls short of the safety threshold by a second measurement value, not create the reconditioning profile, wherein the second measurement value is greater than the first measurement value.

4. The system of claim 2, wherein the configuration to create a reconditioning profile further comprises instructions that may be executed by the processor to compare the set of image data to a set of new device image data and determine a level of deformity of the end effector of the used surgical instrument.

5. system of claim 1, further comprising a load cell configured to receive an end effector of the used surgical instrument during the post-procedure reconditioning process, wherein the configuration to create a reconditioning profile further comprises instructions that may be executed by the processor to cause:
   (i) the end effector to activate and apply a force to the load cell,
   (ii) the load cell to measure the force, and
   (iii) the end effector to cease applying the force to the load cell such that it can be disengaged from the load cell.

6. The system of claim 1, further comprising a display, wherein the display is configured to display the reconditioning profile, and wherein the processor is further configured to receive a user selection indicating that the reconditioning profile should be applied to the used surgical instrument.

7. The system of claim 6, further comprising a network device in communication with a remote server, wherein the network device is configured to transmit the user selection to the remote server, and wherein the network device is further configured to transmit a notification to the remote server when one or more of the set of surgical instrument modes are enabled.

8. The system of claim 1, wherein the set of usage data comprises:
   (A) a surgical instrument activation count associated with the used surgical instrument,
   (B) a surgical instrument activation duration count associated with the used surgical instrument,
   (C) a surgical instrument generator connection duration count associated with the used surgical instrument, and
   (D) a surgical instrument close cycle count associated with the used surgical instrument; and
   wherein the set of electrical characteristics comprises:
   (A) capacitance associated with the used surgical instrument,
   (B) power consumption associated with the used surgical instrument, and
   (C) phase margin associated with the used surgical instrument.

9. The system of claim 1, wherein the reconditioning profile comprises:
   (A) a surgical instrument reconfiguration, wherein the surgical instrument reconfiguration is configured to be written to a memory of the used surgical instrument to modify operation of the used surgical instrument, and
   (B) a surgical instrument activation dataset, wherein the surgical instrument activation dataset is configured to be written to the memory of the used surgical instrument to enable one or more of the set of surgical instrument modes.

10. A method comprising the steps of:
   (a) at a reconditioning device, reading a set of usage data from a used surgical instrument;
   (b) attaching the used surgical instrument to an input actuator of the reconditioning device, wherein the input actuator is operable to activate an instrument trigger of the used surgical instrument, and activating one or more of a set of surgical instrument modes of the used surgical instrument via the input actuator and measuring a set of electrical characteristics of the used surgical instrument during activation;
   (c) measuring a set of mechanical characteristics of the used surgical instrument via the reconditioning device;
   (d) creating, based upon the set of usage data, the set of electrical characteristics, and the set of mechanical characteristics, a reconditioning profile that may be applied to the used surgical instrument by the reconditioning device;

(e) receiving a user input indicating that the reconditioning profile should be applied to the used surgical instrument; and
(f) applying the reconditioning profile to the used surgical instrument in response to the user input, wherein applying the reconditioning profile to the used surgical instrument enables one or more of the set of surgical instrument modes;
wherein the reconditioning device is used during a post-procedure reconditioning process.

11. The method of claim 10, wherein the step of measuring the set of electrical characteristics of the used surgical instrument comprises one or more of the following acts:
(i) measuring acoustic impedance of an ultrasonic blade of the used surgical instrument,
(ii) measuring the conductivity of an activation circuit of the used surgical instrument, or
(iii) measuring at least one of capacitance, power consumption, or phase shift margin of a transducer of the used surgical instrument.

12. The method of claim 10, wherein the reconditioning profile comprises a surgical instrument reconfiguration, the method further comprising writing the surgical instrument reconfiguration to a memory of the used surgical instrument to modify the electrical characteristics of the used surgical instrument during activation.

13. The method of claim 10, wherein the step of measuring the set of mechanical characteristics of the used surgical instrument comprises one or more of the following acts performed during a post-procedure reconditioning process:
(i) measuring force applied by an end effector of the used surgical instrument to a load cell of the reconditioning device,
(ii) measuring thickness of a clamp pad of the end effector with an imaging device of the reconditioning device, or
(iii) measuring deformity of the end effector with an imaging device of the reconditioning device.

14. The method of claim 13, further comprising the steps of, if the force applied by the end effector the load cell does not fall between a minimum force threshold and a maximum force threshold:
(a) terminating the creation of the reconditioning profile; and
(b) indicating to a user that reconditioning of the surgical instrument is not possible.

15. The method of claim 13, further comprising the steps of, if the thickness of the clamp pad of the end effector does not fall between a minimum thickness threshold and a maximum thickness threshold:
(a) terminating the creation of the reconditioning profile; and
(b) indicating to a user that reconditioning of the surgical instrument is not possible.

16. The method of claim 13, further comprising the steps of, if the end effector displays unsafe deformity relative to a new end effector:
(a) terminating the creation of the reconditioning profile; and
(b) indicating to a user that reconditioning of the surgical instrument is not possible.

17. The method of claim 10, further comprising the steps of:

(a) displaying the reconditioning profile to a user via a display of the reconditioning device;
(b) displaying a set of conditions to the user via the display, the set of conditions indicating a cost associated with applying the reconditioning profile to the used surgical instrument; and
(c) after receiving the user input indicating that the reconditioning profile should be applied to the used surgical instrument, sending a purchase signal to a remote server via a network device of the reconditioning device identifying the user, the used surgical instrument, and the reconditioning profile.

18. A system comprising:
(a) a used surgical instrument comprising:
(i) an instrument trigger,
(ii) an end effector, the end effector comprising an ultrasonic blade and a clamp arm, the clamp having a clamp pad,
(iii) a generator connection, and
(iv) a surgical instrument body, and
(b) a reconditioning device comprising:
(i) a surgical instrument holder, wherein the surgical instrument holder is configured to hold the surgical instrument body,
(ii) a generator configured to couple with the generator connection, wherein the generator is configured to:
(A) provide power to the used surgical instrument,
(B) receive data from the used surgical instrument, and
(C) transmit data to the used surgical instrument,
(iii) a surgical instrument actuator configured to actuate the instrument trigger and thereby activate the end effector during a post-procedure reconditioning process,
(iv) an imaging device positioned to capture an image of the end effector,
(v) a load cell configured to receive and measure a clamping force of the clamp arm during the post-procedure reconditioning process, and
(vi) a memory, wherein the memory is configured to store a set of instructions, and
(vii) a processor, wherein the processor is configured to execute the instructions to, during the post-procedure reconditioning process:
(A) receive a set of usage data from the used surgical instrument,
(B) cause the surgical instrument actuator to activate the used surgical instrument in a first mode,
(C) while the first mode is active, measure a set of electrical characteristics of the used surgical instrument,
(D) based upon the set of usage data, the set of electrical characteristics, end effector structural characteristics as visualized by the imaging device, and the clamping force, create a reconditioning profile that may be applied to the used surgical instrument,
(E) apply the reconditioning profile to the used surgical instrument, thereby enabling at least one operational mode of the used surgical instrument.

* * * * *